(12) United States Patent  
Gripp

(10) Patent No.: US 6,962,083 B2  
(45) Date of Patent: Nov. 8, 2005

(54) DEVICES FOR THE ULTRASONIC TESTING OF A WORKPIECE BY THE TRANSMISSION TECHNIQUE

(75) Inventor: Sebastian Gripp, Alzenau (DE)

(73) Assignee: IntelligeNDT Systems & Services GmbH & Co. KG, Erlangen (DE)

( * ) Notice: Subject to any disclaimer, the term of this patent is extended or adjusted under 35 U.S.C. 154(b) by 15 days.

(21) Appl. No.: 10/755,922

(22) Filed: Jan. 12, 2004

(65) Prior Publication Data

US 2004/0139802 A1    Jul. 22, 2004

(30) Foreign Application Priority Data

Jan. 10, 2003   (DE) ................................. 103 00 827

(51) Int. Cl.$^7$ ......................... G01N 29/08; G01N 29/26
(52) U.S. Cl. ........................... 73/618; 73/599; 73/633; 901/44
(58) Field of Search .................... 73/618, 599, 600, 73/597, 598, 633; 901/44

(56) References Cited

U.S. PATENT DOCUMENTS

| 4,106,327 A | * | 8/1978 | Adler et al. | ................... 73/618 |
| 4,881,177 A |   | 11/1989 | McClean et al. | ........... 700/258 |
| 2002/0148295 A1 |   | 10/2002 | Shives et al. | ................. 73/618 |

FOREIGN PATENT DOCUMENTS

| EP | 0 444 578 A2 | 9/1991 |
| EP | 0 852 721 B1 | 7/1998 |

* cited by examiner

*Primary Examiner*—John E. Chapman  
(74) *Attorney, Agent, or Firm*—Laurence A. Greenberg; Wenrer H. Stemer; Ralph E. Locher

(57) ABSTRACT

A device for the free-jet ultrasonic testing of a workpiece by the transmission technique includes a first test head, serving as an ultrasound transmitter, and a second test head, serving as an ultrasound receiver. The test heads are respectively disposed on a first robot and a second robot, in each case in a freely movable manner, with at least one degree of freedom, such that they are aligned coaxially in relation to each other and perpendicular to a surface of a workpiece. The robots are positioned such that they are fixed in place on a displaceable common carrier.

10 Claims, 2 Drawing Sheets

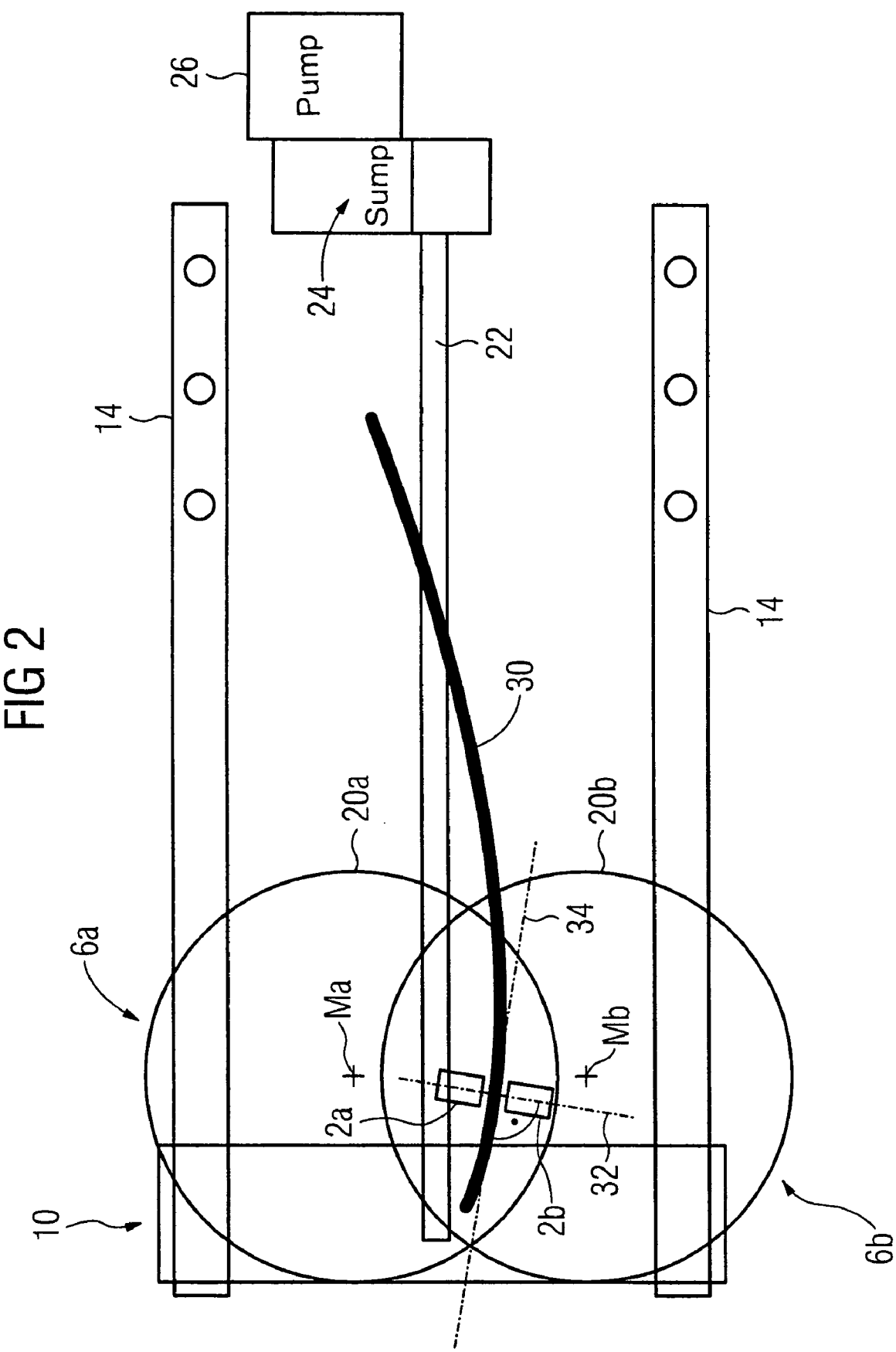

DEVICES FOR THE ULTRASONIC TESTING OF A WORKPIECE BY THE TRANSMISSION TECHNIQUE

BACKGROUND OF THE INVENTION

Field of the Invention

The invention relates to a device for the ultrasonic testing of a workpiece by the transmission technique.

Instead of a pulse-echo technique that is frequently used in ultrasonic testing, it is of advantage for detecting defects near the surface and for testing components made of so-called sandwich material (honeycombed core with thin outer layers of fiber-reinforced plastic) to carry out a transmission technique, in which the workpiece is located between a test head serving as the ultrasound transmitter and a test head serving as the ultrasound receiver.

In the ultrasonic testing of a workpiece by the transmission technique, in many applications the ultrasound test signals are transmitted between the test heads and the workpiece in a free water jet (free jet technique) or by air. Such a testing technique, which is also referred to as the squirter technique, is intended, in particular, for the testing of complexly shaped and large components that cannot be tested by immersion in a water bath. A test head suitable for the squirter technique is known, for example, from European Patent Application EP 0 444 578 A2.

In ultrasonic testing by the transmission technique, it is necessary for the test heads lying opposite each other to be always aligned coaxially in relation to each other, the deviation from coaxiality not being allowed to exceed 1 mm.

SUMMARY OF THE INVENTION

It is accordingly an object of the invention to provide a device for the ultrasonic testing of a workpiece by the transmission technique that overcomes the hereinafore-mentioned disadvantages of the heretofore-known devices of this general type and that can also be used for workpieces of a large area with a complicated surface shape.

With the foregoing and other objects in view, there is provided, in accordance with the invention, a device for the ultrasonic testing of a workpiece by the transmission technique, including first and second robots, first and second test heads, one of the first and second test heads being an ultrasound transmitter and the other of the first and second test heads being an ultrasound receiver, the first and second test heads being respectively disposed on the first and second robots in a freely movable manner with at least one degree of freedom to coaxially align with respect to one another and perpendicular to a surface of the workpiece, and a displaceable bracket on which the first and second robots are fixed.

According to the invention of the instant application, a first test head, serving as an ultrasound transmitter, is disposed on a first robot and a second test head, serving as an ultrasound receiver, is disposed on a second robot, in each case in a freely movable manner, with at least one degree of freedom, such that they are aligned coaxially in relation to each other and perpendicular to a surface of a workpiece. The first and second robots are, respectively, positioned such that they are fixed in place on a displaceable bracket.

Such a configuration permits the testing of workpieces of a large area along a test path of a linear form that can vary according to the number of degrees of freedom of the robot.

In accordance with another feature of the invention, the displaceable brackets can be fixed such that they are fixed in place on a common carrier. In other words, the first and second robots are disposed in a fixed relationship with respect to each other.

The fixed-in-place positioning of the first and second robots on a common carrier ensures that the position of the origin of the coordinates of the movement of the first test head that is brought about by the first robot is always the same in relation to the position of the origin of the coordinates of the movement of the second test head that is brought about by the second robot. In other words, considered from the origin of the coordinates of one robot, the origin of the coordinates of the other robot is always at the same position so that even a traveling movement of the carrier required for workpieces of a large area does not cause a relative movement of the origins of the coordinates. Such a rigid connection of the robot bases has the effect of significantly reducing the requirements imposed on the capabilities of the robot control because, now, only a synchronization or coordination of the movement is required for the number of degrees of freedom with which the test head can be moved by the robot itself.

In accordance with a further feature of the invention, the carrier defines a measuring space for receiving the workpiece, is a bridge spanning the measuring space, and has mutually opposite supports, and the brackets are disposed on the supports.

In accordance with an added feature of the invention, the brackets are adjustably disposed in predetermined positions on the supports.

In accordance with an additional feature of the invention, there are provided rails. The supports can be guided at or in the rails.

Because the requirements imposed on the control increase with every additional degree of freedom, the invention is of advantage, in particular, when multi-axial robots are used.

In accordance with yet another feature of the invention, a six-axis robot is provided for each test head, allowing the two test heads to be guided over the workpiece along a curve of a path that can be freely predetermined spatially (3 degrees of freedom) while retaining their coaxial alignment and alignment perpendicular to the surface of the workpiece (a further 3 degrees of freedom). Such a configuration permits the testing of workpieces with complex shapes.

In accordance with yet a further feature of the invention, there is provided a common carrier. The displaceable bracket is configured to fix in place on the common carrier.

With the objects of the invention in view, there is also provided a device for the ultrasonic testing of a workpiece by the transmission technique, including first and second robots, first and second test heads, one of the first and second test heads being an ultrasound transmitter and one the first and second test heads being an ultrasound receiver, the first and second test heads being respectively disposed on the first and second robots in a freely movable manner with at least one degree of freedom to coaxially align with respect to one another and perpendicular to a surface of the workpiece, and a displaceable bracket on which the first and second robots are fixed.

Other features that are considered as characteristic for the invention are set forth in the appended claims.

Although the invention is illustrated and described herein as embodied in a device for the ultrasonic testing of a workpiece by the transmission technique, it is, nevertheless, not intended to be limited to the details shown because various modifications and structural changes may be made therein without departing from the spirit of the invention and within the scope and range of equivalents of the claims.

The construction and method of operation of the invention, however, together with additional objects and advantages thereof, will be best understood from the following description of specific embodiments when read in connection with the accompanying drawings.

BRIEF DESCRIPTION OF THE DRAWINGS

FIG. 2 is a plan view of the device of FIG. 1 with a workpiece located therein.

DESCRIPTION OF THE PREFERRED EMBODIMENTS

Figure 1:
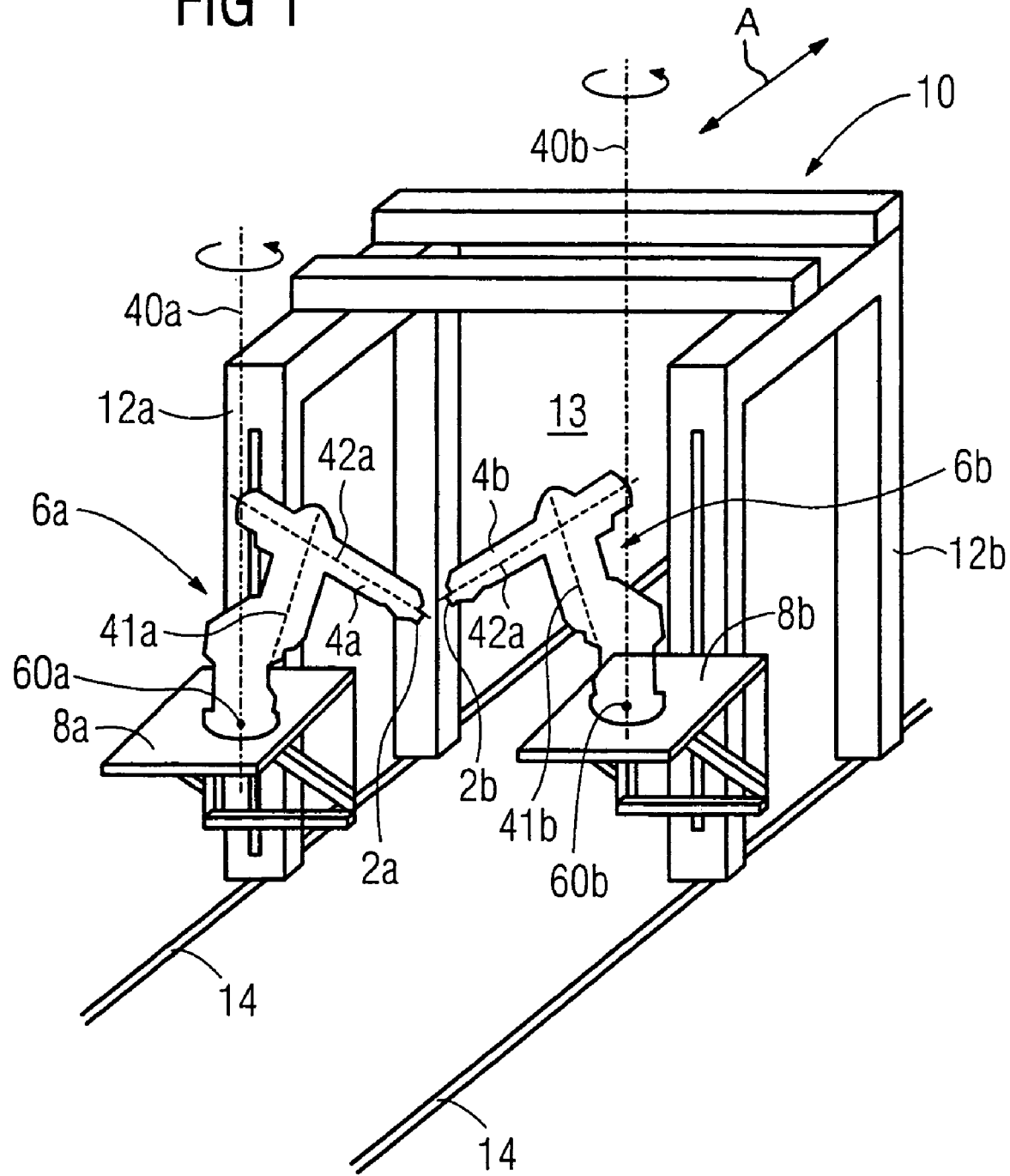
FIG. 1 is a fragmentary, perspective view of a device according to the invention.

Referring now to the figures of the drawings in detail and first, particularly to FIG. 1 thereof, there is shown a first test head 2a located at the end of the arm 4a of a six-axis first robot 6a and a second test head 2b is located at the end of the arm 4b of a second, likewise six-axis, robot 6b. One of the two test heads 2a, 2b serves as an ultrasound transmitter, while the other test head 2b or 2a serves as a receiver. The arms 4a, 4b are mounted in a two-jointed and rotatable manner about a vertical axis 40a or 40b, respectively. At the free end of the arms 4a, 4b, the test head 2a or 2b is respectively mounted such that it can pivot about three hand axes so that the test heads 2a, 2b can be displaced along a spatially freely predeterminable test path on mutually opposite surfaces of a workpiece curved in any desired way, while retaining their coaxial alignment and alignment perpendicular to the surface of the workpiece. In FIG. 1, the respective joints 41a, 42a and 41b, 42b of the arms 4a, 4b are indicated by dashed lines.

The first and second test heads 2a, 2b are so-called free-jet ultrasound test heads, with which the ultrasound propagates between the workpiece to be tested and the test head in a free water jet. Alternatively, with appropriate heads (transducers), the sound propagation may also take place through air. To permit ultrasonic testing by the transmission technique, it is necessary to align the test heads 2a, 2b exactly with each other during the measurement and to maintain such coaxial alignment even when the test heads 2a, 2b are being displaced along the test path, i.e., the movement of the robots 6a, 6b must take place in a synchronized or coordinated manner.

To extend the testing volume, i.e., the spectrum of sizes and shapes of possible test pieces, beyond the range (working cell) of a single robot, each robot 6a, 6b is mounted with its base 60a or 60b on a displaceable bracket 8a, 8b. The brackets 8a, 8b are fixed on a common carrier 10. The carrier 10 is formed in the exemplary embodiment by a bridge with two supports 12a, 12b, which spans a measuring space 13 for receiving a workpiece. The brackets 8a, 8b are disposed in a height-adjustable manner in predetermined positions (engaged positions) on mutually opposite supports 12a or 12b, to allow workpieces of a height that exceeds the radius of action of the robots 6a, 6b also to be tested. In addition, horizontal adjustability of the brackets 8a, 8b may also be provided, to allow the range of the robots to be adapted to the respective workpiece. During the measurement, i.e., during the traveling movement of the test heads 2a, 2b along a predetermined test path, the brackets 8a, 8b are fixed such that they are fixed in place on the carrier 10.

The supports 12a, 12b are guided in rails 14 so that the carrier 10 and, consequently, the brackets 8a, 8b, can be displaced linearly, as illustrated in FIG. 1 by a double-headed arrow A. In the case of such traveling movement, the relative position of the robot bases 6a, 6b is retained, so that (with a linear movement of the support 10) one degree of freedom less has to be coordinated in the control of the two robots 6a, 6b. Consequently, in the exemplary embodiment; the linear movement of the carrier 10 jointly displaces the brackets 8a, 8b. As an alternative thereto, individual displaceability of the brackets and, consequently, of the robot bases, may also be provided. Then, the complexity of the control for the coordination of movements is increased correspondingly.

In the plan view according to FIG. 2, the radii of action of the first and second robots 6a, 6b are indicated by circles 20a, 20b. The center points Ma, Mb of these circles 20a, 20b are in a fixed position in relation to each other, i.e., their relative position does not change during the traveling movement of the carrier 10. It can also be seen in FIG. 2 that between the rails 14 there runs a collecting channel 22, which collects water respectively emerging from the test heads 2a, 2b and feeds it to a sump 24, from which it is pumped away with the aid of a pumping station 26.

Disposed between the first and second test heads 2a, 2b is a workpiece 30 to be investigated, which is made to extend in the longitudinal direction. The first and second test heads 2a, 2b are aligned coaxially with respect to each other (transmitting and receiving center axes 32 coincide) and perpendicular to the surface of the workpiece 30 (transmitting and receiving center axes 32 are perpendicular to tangent 34) during the testing so that the water jet of the first test head 2a, serving, for example, as an ultrasound transmitter, impinges on the workpiece 30 at a point which lies opposite the point of impingement of the water jet of the second test head 2b, serving as an ultrasound receiver. The use of six-axis robots 6a, 6b allows workpieces 30 that have surfaces that are greatly curved about multiple axes also to be tested.

I claim:

1. A device for the ultrasonic testing of a workpiece by the transmission technique, comprising:
    first and second robots;
    first and second test heads;
    one of said first and second test heads being an ultrasound transmitter and the other of said first and second test heads being an ultrasound receiver;
    said first and second test heads being respectively disposed on said first and second robots in a freely movable manner with at least one degree of freedom to coaxially align with respect to one another and perpendicular to a surface of the workpiece; and
    a displaceable bracket on which said first and second robots are fixed.

2. The device according to claim 1, wherein said bracket is a plurality of said displaceable brackets and further comprising a common carrier on which said displaceable brackets are fixed in place.

3. The device according to claim 2, wherein:
said carrier defines a measuring space for receiving the workpiece, is a bridge spanning said measuring space, and has mutually opposite supports; and
said brackets are disposed on said supports.

4. The device according to claim 3, wherein said brackets are adjustably disposed in predetermined positions on a respective one of said supports.

5. The device according to claim 4, further comprising rails, said supports being guided in said rails.

6. The device according to claim 1, wherein said first and second robots are six-axis robots.

7. The device according to claim 1, further comprising a common carrier, said displaceable bracket being configured to fix in place on said common carrier.

8. The device according to claim 7, wherein:
said carrier defines a measuring space for receiving the workpiece, is a bridge spanning said measuring space, and has mutually opposite supports; and
said brackets are disposed on said supports.

9. The device according to claim 8, wherein said brackets are adjustably disposed in predetermined positions on said supports.

10. The device according to claim 9, further comprising rails, said supports being guided at said rails.

* * * * *